US012799459B2

(12) United States Patent
Ochiya et al.

(10) Patent No.: US 12,799,459 B2
(45) Date of Patent: Nov. 17, 2026

(54) METHOD FOR PRODUCING STEM/PRECURSOR CELLS, BY USING LOW MOLECULAR WEIGHT COMPOUND, FROM CELLS DERIVED FROM ENDODERMAL TISSUE OR ORGAN

(71) Applicant: Evia Life Sciences Inc., Seattle, WA (US)

(72) Inventors: Takahiro Ochiya, Tokyo (JP); Juntaro Matsuzaki, Tokyo (JP); Hideharu Enomoto, Tokyo (JP); Masumi Shinohara, Tokyo (JP)

(73) Assignee: Evia Life Sciences Inc., Seattle, WA (US)

( * ) Notice: Subject to any disclaimer, the term of this patent is extended or adjusted under 35 U.S.C. 154(b) by 990 days.

(21) Appl. No.: 17/285,038

(22) PCT Filed: Oct. 11, 2019

(86) PCT No.: PCT/JP2019/041234

§ 371 (c)(1),
(2) Date: Apr. 13, 2021

(87) PCT Pub. No.: WO2020/080550

PCT Pub. Date: Apr. 23, 2020

(65) Prior Publication Data

US 2021/0403874 A1 Dec. 30, 2021

(30) Foreign Application Priority Data

Oct. 15, 2018 (JP) ................................ 2018-194567

(51) Int. Cl.
*C12N 5/071* (2010.01)
*A61K 35/39* (2015.01)
*G01N 33/50* (2006.01)

(52) U.S. Cl.
CPC ............ *C12N 5/0678* (2013.01); *A61K 35/39* (2013.01); *G01N 33/5014* (2013.01); *G01N 33/5073* (2013.01); *C12N 2501/15* (2013.01); *C12N 2501/727* (2013.01); *C12N 2533/54* (2013.01)

(58) Field of Classification Search
CPC .............. C12N 5/0678; C12N 2501/15; C12N 2501/727; A61K 35/39; G01N 33/5073
See application file for complete search history.

(56) References Cited

U.S. PATENT DOCUMENTS 4,997,834 A 3/1991 Muro
7,199,147 B2 4/2007 Imazaki
7,217,722 B2 5/2007 Takami
9,909,105 B2 * 3/2018 Lin ...................... C12N 5/0696
10,655,105 B2 * 5/2020 Kunisada ............ C12N 5/0676
10,961,507 B2 3/2021 Ochiya
11,149,253 B2 * 10/2021 Wang .................. C12N 5/0679
2003/0220357 A1 11/2003 Bankston
2003/0228689 A1 12/2003 Freier
2004/0115641 A1 6/2004 Cowsert et al.
2005/0182040 A1 8/2005 Imazaki
2005/0197328 A1 9/2005 Bailey
2006/0241127 A1 10/2006 Feurer
2011/0243903 A1 10/2011 Mcbride
2012/0021519 A1 1/2012 Ichida
2012/0264218 A1 10/2012 Lin
2012/0282228 A1 11/2012 Bhasin
2013/0071931 A1 3/2013 Ishikawa
2013/0109092 A1 5/2013 Matsuyama
2013/0264218 A1 10/2013 Vinton
2013/0344594 A1 12/2013 Rust
2014/0220681 A1 * 8/2014 Valamehr ............. C12N 5/0607 435/377
2015/0231181 A1 8/2015 Rust
2015/0240214 A1 8/2015 Lin
2016/0145581 A1 * 5/2016 Deng .................. A61K 35/545 435/377
2016/0206664 A1 7/2016 Sokal
2017/0233700 A1 8/2017 Kunisada
2018/0042847 A1 2/2018 Ross
2019/0010464 A1 1/2019 Ochiya
2019/0302100 A1 * 10/2019 Katsuda ............... C12N 5/0672
2020/0283763 A1 9/2020 Hong
2021/0403874 A1 12/2021 Ochiya
(Continued)

FOREIGN PATENT DOCUMENTS

AU 2017205801 8/2018
CN 102027105 4/2011
(Continued)

OTHER PUBLICATIONS

Lima, Maria João, et al. "Suppression of epithelial-to-mesenchymal transitioning enhances ex vivo reprogramming of human exocrine pancreatic tissue toward functional insulin-producing β-like cells." Diabetes 62.8 (2013): 2821-2833. (Year: 2013).*
Zaret, Kenneth S., and Markus Grompe. "Generation and regeneration of cells of the liver and pancreas." Science 322.5907 (2008): 1490-1494. (Year: 2008).*
Li, et al., "Small Molecules Facilitate the Reprogramming of Mouse Fibroblasts into Pancreatic Lineages", Cell Stem Cell, 14(2): 228-236 (2014).
Ariyachet et al., "Reprogrammed Stomach Tissue as a Renewable Source of Functional β Cells for Blood Glucose Regulation", Cell Stem Cell. Mar. 3, 2016; 18(3): 410-421.
Dai et al., "Direct Reprogramming by Small Molecules for Regenerative Medicine," Total Memory, 2018, 127(1), 12 pages (with English abstract).
(Continued)

*Primary Examiner* — Teresa E Knight
*Assistant Examiner* — Michael Angelo Riga
(74) *Attorney, Agent, or Firm* — Pabst Patent Group LLP

(57) ABSTRACT

The present invention provides a method starting from cells derived from a mammalian endodermal tissue or organ (except for the liver) to produce stein/progenitor cells thereof, which comprises bringing the cells derived from the endodermal tissue or organ into contact in vitro with a TGFβ-receptor inhibitor.

18 Claims, 9 Drawing Sheets

(56) References Cited

U.S. PATENT DOCUMENTS

| | | | |
|---|---|---|---|
| 2024/0425816 A1 | 12/2024 | Ochiya et al. |
| 2025/0235484 A1 | 7/2025 | Ochiya |

FOREIGN PATENT DOCUMENTS

| | | |
|---|---|---|
| CN | 103380212 | 10/2013 |
| CN | 104640979 | 5/2015 |
| CN | 106795487 | 5/2017 |
| EP | 2488630 | 8/2012 |
| EP | 2532741 | 12/2012 |
| EP | 2655601 | 10/2013 |
| EP | 2864473 | 4/2015 |
| EP | 3031905 | 6/2016 |
| EP | 3178924 | 6/2017 |
| JP | 08163996 | 6/1996 |
| JP | 08308562 | 11/1996 |
| JP | 2013-507932 | 3/2013 |
| JP | 2014/501108 | 1/2014 |
| JP | 2015-522281 | 8/2015 |
| JP | 2019521669 A | 8/2019 |
| WO | 9806433 | 2/1998 |
| WO | 03059913 | 7/2003 |
| WO | 03062225 | 7/2003 |
| WO | 03062227 | 7/2003 |
| WO | 03064397 | 8/2003 |
| WO | 2004112719 | 12/2004 |
| WO | 2005003101 | 1/2005 |
| WO | WO 2007/039986 | 4/2007 |
| WO | 2008063675 | 5/2008 |
| WO | 2010033906 | 3/2010 |
| WO | 2010057039 | 5/2010 |
| WO | 2011047300 | 4/2011 |
| WO | 2012087965 | 6/2012 |
| WO | 2013018851 | 2/2013 |
| WO | 2013163739 | 11/2013 |
| WO | 2013174794 | 11/2013 |
| WO | 2014004341 | 1/2014 |
| WO | 2014044646 | 3/2014 |
| WO | 2014058080 | 4/2014 |
| WO | 2014201167 | 12/2014 |
| WO | 2015028577 | 3/2015 |
| WO | WO 2016/021734 | 2/2016 |
| WO | 2017019702 | 2/2017 |
| WO | WO2017119512 | 7/2017 |
| WO | 2017177163 | 10/2017 |
| WO | 2017206837 A1 | 12/2017 |
| WO | 2018039986 | 3/2018 |
| WO | WO2018079714 | 5/2018 |
| WO | 2018136005 | 7/2018 |
| WO | 2019043709 | 3/2019 |
| WO | 2020080550 | 4/2020 |
| WO | 2021092657 A1 | 5/2021 |
| WO | 2022080455 | 4/2022 |

OTHER PUBLICATIONS

Huch et al., "Unlimited in vitro expansion of adult bi-potent pancreas progenitors through the Lgr5/R-spondin axis" The EMBO Journal (2013) 32, 2708-2721.

Katsuda et al., "Generation of chemically induced liver progenitors (CLiPs) from rat adult hepatocytes," Bio-Protocol, Jan. 20, 2018, 8(2):e2689, 26 pages.

Katsuda et al., "Conversion of Terminally Committed Hepatocytes to Culturable Bipotent Progenitor Cells with Regenerative Capacity" 2017, Cell Stem Cell 20, 41-55, Jan. 5, 2017, Elsevier Inc.

Katsuda et al., "In vitro reprogramming of mature hepatocytes to culturable liver progenitor cells and their potential application to regenerative medicine", 2018, 7 pages.

Kawamata et al., "Generation of genetically modified rats from embryonic stem cells", PNAS, Aug. 10, 2010, vol. 107, No. 32, 14223-14228.

Li et al., "Long-term persistence and development of induced pancreatic beta cells generated by lineage conversion of acinar cells", Nature Biotechnology, vol. 32, No. 12, Dec. 2014.

Matsuzaki et al., "Low molecular weight compounds induce pancreatic exocrine cells into pancreatic progenitor-like cells and insulin-secreting cells", The 18th Congress of the Japanese Society for Regenerative Medicine, [O-33-3] Oral Presentation 33, Pancreas 2, Mar. 23, 2019, (Saturday).

Matsuzaki et al., "Low molecular weight compounds reprogram pancreatic exocrine cells into pancreatic progenitor-like cells", The 17th Congress of the Japanese Society for Regenerative Medicine [O-47-4] Oral Presentation 47 Liver and Pancreas 4, Mar. 23, 2018 (Friday), 14:00-15:00, Fourth Venue 502 Fourth Venue.

Pagliuca et al., "Generation of functional human pancreatic β cells in vitro", Cell., Oct. 9, 2014, 159(2), 428-39.

PCT International Search Report and Written Opinion in International Appln. No. PCT/JP2019/041234, dated Dec. 24, 2019, 18 pages (with English translation).

Reichert et al., "Culturing primary mouse pancreatic ductal cells," Cold Spring Harbor Protocols, Jun. 1, 2015, (6):558-61.

Wang et al., "Conversion of Human Gastric Epithelial Cells to Multipotent Endodermal Progenitors using Defined Small Molecules", 2016, Cell Stem Cell 19, 449-461, Oct. 6, 2016, Elsevier Inc.

Yoshibara et al., "ERRγ Is Required for the Metabolic Maturation of Therapeutically Functional Glucose-Responsive β Cells", Cell Metabolism 23, 622-634, Apr. 12, 2016.

Zhu et al., "Human pancreatic beta-like cells converted from fibroblasts", Nature Communications, 7:10080, DOI: 10.1038/ncomms10080, www.nature.com/naturecommunications, Jan. 16, 2016.

Anderson, et al., "Prolonging culture of primary human keratinocytes isolated from suction blisters with the Rho kinase inhibitor Y-27632", PLoS ONE, 13(9):e0198862, 1-12 (2018).

Baraniak, et al., "Stem cell paracrine actions and tissue regeneration", Regen Med. 5(1):121-43 (2010).

Beesley, et al., "Lymphedema after gynecological cancer treatment", Cancer, 109:2607-2614 (2007).

Bruno, et al., "Extracellular Vesicles: A Therapeutic Option for Liver Fibrosis", Int. J. Mol. Sci., 21(12):4255 (2020).

Bruno, et al., "Mesenchymal stem cell-derived microvesicles protect against acute tubular injury", J. Am. Soc. Nephrol., 20(5):1053-67 (2009).

Cai, et al., "Directed differentiation of human embryonic stem cells into functional hepatic cells", Hepatology, 45(5):1229-1239 (2007).

Chakraborty, et al., "MicroRNA signature of inflamed lymphatic endothelium and role of miR-9 in lymphangiogenesis and inflammation", Am. J. Physiol. Cell Physiol., 309(10):C680-92 (2015).

Chapman, et al., "The effect of Rho kinase inhibition on long-term keratinocyte proliferation is rapid and conditional", Stem Cell Research & Therapy, 5(60):1-11 (2014).

Chen, et al., "Abstract 188: Hepatocyte exosomes attenuate hepatic stellate cell activation in vitro and are anti-fibrotic in vivo", Hepatology; AASLD Abstracts, John Wiley & Sons, Inc, US, 64, No. SI, Oct. 1, 2016 (Oct. 1, 2016), p. 99A.

Chen, et al., "Mature Hepatocytes Exhibit Unexpected Plasticity by Direct Dedifferentiation into Liver Progenitor Cells in Culture", Hepatology, 55(2):563-574 (2012).

Chen, et al., "Pathways of production and delivery of hepatocyte exosomes", J. of Cell Commun. Signal., 12(13):343-357 (2017).

Chen, et al., "The potential of using itaconate as treatment for inflammation-related heart diseases", Tzu-Chi Med J., 32(2):113 (2019).

Cho, et al., "Skin Brightening E_ cacyf Exosomes Derived from Human Adipose Tissue-Derived Stem/Stromal Cells: A Prospective, Split-Face, Randomized Placebo-Controlled Study", Cosemtics, 7(90):1-12 (2020).

Connor, et al., "Manganese superoxide dismutase enhances the invasive and migratory activity of tumor cells", Cancer Res., 67:10260-10267 (2007).

Conrad, et al., "Multipotent mesenchymal stem cells acquire a lymphendothelial phenotype and enhance lymphatic regeneration in vivo", Circulation, 119(2):281-9 (2009).

(56) References Cited

OTHER PUBLICATIONS

Dai, et al., "Direct Reprogramming by Small Molecules for Regnerative Medicine", Kyoto Prefectural University of Med. vol. 127(1):1-12 (2018).
Dorrell, et al., "Prospective Isolation of a Bipotential Clonogenic Liver Progenitor Cell in Adult Mice", Genes and Development, 25(11): 1193-1203 (2011).
Ebrahim, et al., "MDM2 beyond cancer: podoptosis, development, inflammation, and tissue regeneration", Histol Histopathol., 30(11):1271-1282 (2015).
Extended European Search Report for related application EP Application No. 17736049.2, dated Aug. 16, 2019, 12pages.
Forte, et al., "Lymphaticovenular anastomosis for breast cancer-related upper extremity lymphedema: a literature review", Gland Surg., 9(2):539-544 (2020).
Gandham, et al., "Effects of Y27632 on keratinocyte procurement and wound healing", Clin. Exp. Dermatol., 38(7):782-786 (2013).
Gong, et al., "Mesenchymal stem cells release exosomes that transfer miRNAs to endothelial cells and promote angiogenesis", Oncotarget, 8(28):45200-45212 (2017).
Ha, et al., "Exosomes as therapeutic drug carriers and delivery vehicles across biological membranes: current perspectives and future challenges", Acta Pharmaceutica Sinica B, 6(4):287-296 (2016).
Ha, et al., "Mesenchymal Stem/Stromal Cell-Derived Exosomes for Immunomodulatory Therapeutics and Skin Regeneration", Cells, 9(1157):1-45 (2020).
Hou, et al., "Pluripotent Stem Cells Induced from Mouse Somatic Cells by Small-Molecule Compounds", Science, 341(6146):651-654 (2013).
Huang, et al., "Induction of functional hepatocyte-like cells from mouse fibroblasts by defined factors", Nature, 475:386-389, with Online Methods (lp). (2011).
Ikenoya, et al., "Inhibition of rho-kinase-induced myristoylated alanine-rich C kinase substrate (MARCKS) phosphorylation in human neuronal cells by H-1152, a novel and specific Rho-kinase inhibitor", J. Neurochem. 81(1):9-16 (2002).
International Preliminary Report on Patentability for related application International Application No. PCT/JP2017/000342, Jun. 13, 2018, 15 pages (with translation).
International Search Report for related application International Application No. PCT/JP2017/000342, dated Jul. 13, 2017, 4 pages.
Jeltsch, et al., "Hyperplasia of lymphatic vessels in VEGF-C transgenic mice", Science, 276(5317):1423-5 (1997).
Jennewin, et al., "MicroRNA-27b contributes to lipopolysaccharide-mediated peroxisome _ proliferator-activated receptor gamma (PPARgamma) mRNA destabilization", J. Biol. Chem., 16:11846-11853 (2010).
Jones, et al., "MicroRNA-1236 Inhibits VEGFR-3 Signaling during Inflammatory Lymphangiogenesis", Arterioscler Thromb Vasc Biol., 32(3):633-642 (2012).
Kamiya, et al., "Maturation of fetal hepatocytes in vitro by extracellular matrices and oncostatin M: induction of tryptophan oxygenase", Hepatology, 35(6):1351-1359 (2002).
Karkkainen, et al., "A model for gene therapy of human hereditary lymphedema", PNAS, 98(22):12677-82 (2001).
Katsuda, et al., "Generation of human hepatic progenitor cells with regenerative and metabolic capacities from primary hepatocytes", eLife 8:e47313:1-31 (2019).
Katsuda, et al., "in vitro reprogrammiong of mature hepatocytes to culturable liver progenitor cells and their potential application to regenrative medicine", Cell Stem Cell vol. 20(1):78-84 (2018b).
Katsuda, et al., "Reprogramming of rat mature hepatocytes to bipotent hepatic stem cells", 21st Annual Meeting of the Japanese Society for the Research of Hepatic Cells, pp. 42-43, Nov. 12, 2014 ( original in Japanese, with translation).
Kim, et al., "Exosomes derived from human umbilical cord blood mesenchymal stem cells stimulates rejuvenation of human skin", Biochem Biophys Res Commun., 493(2):1102-1108 (2017).
Lai, et al., "Exosome secreted by MSC reduces myocardial ischemia/reperfusion injury", Stem Cell Res., 4(3):214-22 (2010).
Lener, et al., "Applying extracellular vesicles based therapeutics in clinical trials—an ISEV position paper", J. Extracellular Vesicles, 4(1):30087 (2015).
Li, "Progress in Exosome Isolation Techniques", Theranostics, 7(3):789-804 (2017).
Li, et al., "Extracellular Vesicles From Hepatocytes are Therapeutic for Toxin-Mediated Fibrosis and Gene Expression in the Liver", Front. Cell Dev. Biol., 7(368):1-16 (2020).
Liang, et al., "Exosomes secreted by mesenchymal stem cells promote endothelial cell angiogenesis by transferring miR-125a", J. Cell Sci., 129(11):2182-9 (2016).
Liu, et al., "Genration of endoderm-derived human induced pluripotent stem cells from primary hepatocytes", Hepatology, 51(5):1810-1819 (2010).
Lv, et al., "Self-Renewal ofHepatoblasts Under Chemically Defined Conditions by Iterative Growth Factor and Chemical Screening", Hepatology, 61(1):337-347 (2014).
Maertens, et al., "Bone marrow-derived mesenchymal stem cells drive lymphangiogenesis", PLoS One, 9(9):e106976 (2014).
Maldonado, et al., "Autologous stem cells for the treatment of post-mastectomy lymphedema: a pilot study", Cytotherapy, 13(10):1249-55 (2011).
Mehta-Ambala, "Neocollagenesis and Neoelastinogenesis: From the Laboratory to the Clinic", J. Cutan. Aesthet. Surg., 9(3): 145-151 (2016).
Miyajima, et al., "Stem/Progenitor Cells in Liver Development, Homeostasis, Regeneration, and Reprogramming", Author Manuscript. Cell Stem Cell, 14: 561-574 (2014).
Nasiri, et al., "Shedding light on the role of keratinocyte-derived extracellular vesicles on skin-homing cells," Stem Cell Research & Therapy, 11(1):421 (2020).
Phinney, et al., "Concise Review: MSC-Derived Exosomes for Cell-Free Therapy", Stem Cells, 35(4):851-858 (2017).
Qian, et al., "MicroRNA-26a promotes tumor growth and angiogenesis in glioma by directly targeting prohibitin", CNS Neurosci Ther., 19(10):804-12 (2013).
Rerknimitr, et al., "The etiopathogenesis of atopic dermatitis: barrier disruption, immunological derangement, and pruritus", Inflamm. Regen., 37:14 (2017).
Russ, et al., "Controlled induction of human pancreatic progenitors produces functional beta-like cells in vitro", The Embo Journal/European Molecular Biology Organization, 34(13):1759-1772 (2015).
Sampaziotis, et al., "Cholangiocytes derived from human induced pluripotent stem cells for disease modeling drug validation", Nature Biotechnology, 33(8):845 (2015).
Sekiya, et al., "Direct conversion of mouse fibroblasts to hepatocyte-like cells by defined factors", Nature, 475(7356):390-393 (2011).
Sharma, et al., "Intrasplenic transplantation of isolated adult rat hepatocytes: sex-reversal and/or suppression of the major constituent isoforms of cytochrome P450", Toxicologic Pathology, 40(1):83-92 (2012).
Shimizu, et al., "Therapeutic lymphangiogenesis with implantation of adipose-derived regenerative cells", J Am Heart Assoc., 1(4):e000877 (2012).
Shweta, et al., "MDM2 regulates hypoxic hypoxia-inducible factor 1α stability in an E3 ligase, proteasome, and PTEN-phosphatidylinositol 3-kinase-AKT-dependent manner", J Biol Chem., 289(33):22785-97 (2014).
Skotland, et al., "Lipids in exosomes: Current knowledge and the way forward", Progress in Lipid Research, 66:30-41 (2017).
Spees, et al., "Mechanisms of mesenchymal stem/stromal cell function", Stem Cell Res Ther., 7:125 (2016).
Sturdwick, et al., "Combination of Low Calcium with Y-27632 Rock Inhibitor Increases the Proliferative Capacity, Expansion Potential and Lifespan of Primary Human Keratinocytes while Retaining Their Capacity to Differentiate into Stratified Epidermis in a 3D Skin Model", Plos One, 1-12 (2015).
Szuba, et al., "Therapeutic lymphangiogenesis with human recombinant VEGF-C", FASEB J., 16(14):1985-7 (2002).

(56) References Cited

OTHER PUBLICATIONS

Tada, et al., "Risk factors for lower limb lymphedema after lymph node dissection in patients with ovarian and uterine carcinoma", BMC Cancer, 9:47 (2009).
Takeda, et al., "Adipose-Derived Stem Cells Promote Proliferation, Migration, and Tube Formation of Lymphatic Endothelial Cells In Vitro by Secreting Lymphangiogenic Factors", Annals of Plastic Surgery, 74(6):728-736 (2015).
Tanaka, et al., "Liver Stem/Progenitor Cells: Their Characteristics and Regulatory Mechanisms", J. of Biochem., 149(3):231-239 (2011).
Tarlow, et al., "Bipotential adult liver progenitors are derived from chronically injured mature hepatocytes", Cell Stem Cell, 15(5):605-618 (2014).
Tashiro, "Lymphangiogenesis induced by exosomes derived from adiposederived mesenchymal stem cells", Database accession No. EMB-627696729 Abstract P12.06 on p. 102 & Journal of Extracellular Vesicles 2019 Taylor and Francis Ltd. NLD, 8(1):102 (2019).
Than, et al., "Differential Expression of Keratinocyte-Derived Extracellular Vesicle Mirnas Discriminate Exosomes From Apoptotic Bodies and Microvesicles", Front. in Endocrinology, 9(535):1-15 (2018).
Thery, et al., "Minimal information for studies of extracellular vesicles 2018 (MISEV2018): a position statement of the International Society for Extracellular Vesicles and update of the MISEV2014 guidelines", J. Extracell. Vesicles, 7(1):1535750 (2018).
Tomizawa, et al., "Single-step protocl for the differentiation of human-induced pluripotent stem cells into hepatic progenitor-like cells", Biomeical Reports, 1.1: 18-22 (2013).
Toyserkani, et al., "Treatment of Breast Cancer-Related Lymphedema with Adipose-Derived Regenerative Cells and Fat Grafts: A Feasibility and Safety Study", Stem Cells Transl Med., (8):1666-1672 (2017).
Valadi, et al., "Exosome-mediated transfer of mRNAs and microRNAs is a novel mechanism of genetic exchange between cells", Nature Cell Biology, 9:654-659 (2007).
Wang, et al., "Exosomes from Adipose-Derived Stem Cells Promotes VEGF-C-Dependent Lymphangiogenesis by Regulating miRNA-132/TGF-[beta] Pathway", Cellular Physiology and Biochemistry, 49(1):160-171 (2018).
Xu, et al., "Mir-27a induced by colon cancer cells in hlecs promotes lymphangiogenesis by targeting smad4", PloS One, 12:e0186718 (2017).
Yahata, et al., "Nuclear translocation of phosphorylated STAT3 is essential for vascular endothelial growth factor-induced human dermal microvascular endothelial cell migration and tube formation", J Biol Chem., 278:40026Y40031 (2003).
Yanez-Mo, et al., "Biological properties of extracellular vesicles and their physiological functions", J. Extracell Vesicles, 4: 27066 (2015).
Yang, et al., "Functional exosome-mimic for delivery of siRNA to cancer: in vitro and in vivo evaluation", J. Control. Release, 243:160-171 (2016).
Yanger et al., "Robust cellular reprogramming occurs spontaneously during liver regeneration", Genes & Development, 27:719-724, 2013, pp. 719-724, with Erratum notice (lp).
Yarrow, et al., "Screening for cell migration inhibitors via automated microscopy reveals a Rho-kinase inhibitor", Chem. Biol. 12(3):385 (2005).
Yoshimura, et al., "Characterization of freshly isolated and cultured cells derived from the fatty and fluid portions of liposuction aspirates", J Cell Physiol. , 208:64-76 (2006).
Zhang, et al., "Exosomes released from human induced pluripotent stem cells-derived MSCs facilitate cutaneous wound healing by promoting collagen synthesis and angiogenesis", J. Transl. Med., 13:49 (2015).
Zhang, et al., "Long-Term in Vitro Expansion of Epithelial Stem Cells Enabled by Pharmalogical Inhibition of PAK1-Rock-Myosin II and TGF-beta Signaling", Cell Rep., 25(3):598610 (2018).
Zhang, et al., "Physiological and pathological impact of exosomes of adipose tissue", Cell Prolif., 49:3-13 (2016).
Zhao, et al., "Exosomes From Adipose-Derived Stem Cells Attenuate Adipose Inflammation and Obesity Through Polarizing M2 Macrophages and Beiging in White Adipose Tissue", Diabetes, 67(2):235-247 (2018).
Zhou, et al., "Long-term persistence and development of induced pancreatic beta cells generated by lineage conversion of acinar cells", Nature Biotechnology, 32(12):1223-1230 (2014).
Zhu, et al., "Mouse liver repopulation with hepatocytes generated from human fibroblasts", Nature, 508(7494):93-97 (2014).
Zuk, et al., "Multilineage cells from human adipose tissue: implications for cell-based therapies", Tissue Eng., 7(2):211-28 (2001).
PCT International Search Report and Written Opinion in International Appln. No. PCT/JP2019/041234, dated Apr. 23, 2020, 9 pages.
Chen, et al., "Immortalization and Characterization of Rat Lingual Keratinocytes in a High-Calcium and Feeder-Free Culture System Using Rock Inhibitor Y-27632", International Journal of Molecular Sciences, vol. 22; 6782, Jun. 24, 2021, pp. 1-17.
Liu, et al., "Exosomes as a Novel Pathway for Regulating Development and Diseases of the Skin (Review)", Biomedical Reports, vol. 8, 2018, pp. 207-214.
Wang, et al., "Exosomes in Chronic Inflammatory Skin Diseases and Skin Tumors", Experimental Dermatology, vol. 28, 2019, pp. 213-218.
Wong, et al., "New Insight into the Role of Exosomes in Vitiligo", Autoimmunity Reviews, 2020, 18 pages.
Yang, et al., "Rock Inhibitor Y-27632 Promotes Proliferation of Human Keratinocytes and Inhibits its Senescence", Chinese Journal of Tissue Engineering Research, vol. 22, No. 24, 2018, pp. 3869-3874.

* cited by examiner

METHOD FOR PRODUCING STEM/PRECURSOR CELLS, BY USING LOW MOLECULAR WEIGHT COMPOUND, FROM CELLS DERIVED FROM ENDODERMAL TISSUE OR ORGAN

TECHNICAL FIELD

The present invention relates to a method for producing stem/progenitor cells using a low molecular weight compound, starting from cells derived from endodermal tissue or organ, and more particularly relates to a method for producing pancreatic stem/progenitor cells using a low molecular weight compound, starting from mature pancreatic exocrine cells, and an inducer comprising such a low molecular weight compound for inducing mature pancreatic exocrine cells into pancreatic stem/progenitor cells, etc.

BACKGROUND ART

Although advances in stem cell biology have aroused great interest in its applications in regenerative medicine, they have not yet been realized. Although induced pluripotent stem cells (iPS cells) are one of the most promising cell sources, there still has been no hope of their application to actual clinical practice due to the remaining presence of tumorigenesis risk (Cell. 2014 Oct. 9; 159(2):428-39) (Cell Metab. 2016 Apr. 12; 23(4): 622-634). Meanwhile, recent study has shown that cells of different lineage can directly be converted (directly reprogrammed) into progenitor cell-like cells, but direct reprogramming is still associated with unexpected risks since it involves genetic modification like iPS cells, and thus cannot be applied to regenerative medicine (Nat Commun. 2016 Jan. 6; 7:10080) (Cell Stem Cell. 2016 Mar. 3; 18(3):410-21) (Nat Biotechnol. 2014 December; 32(12):1223-30).

Recently, there have been reported surprising findings that when the pancreas is injured, proliferative and bipotential pancreatic stem/progenitor cells can be isolated from adult pancreatic exocrine cells (EMBO J. 2013 Oct. 16; 32(20): 2708-21). These innovative findings provide great insight not only to the pancreatic stem cell theory but also to the pancreatic regeneration studies. Specifically, if such reprogramming can be reproduced in vitro, the resulting stem/progenitor cells are expected to serve as a new cell source in regenerative medicine.

However, a method for reprogramming mature cells into stem/progenitor cells without genetic modification is totally unknown.

The inventors of the present invention and other groups have previously reported that a combination of certain types of low molecular weight inhibitors contributes to the induction and maintenance of pluripotency of stem cells (Proc Natl Acad Sci USA. 2010 Aug. 10; 107(32):14223-8) (Cell Stem Cell. 2017 Jan. 5; 20(1):41-55) (Cell Stem Cell. 2016 Oct. 6; 19(4):449-461).

Moreover, the inventors of the present invention have succeeded in producing hepatic stem/progenitor cells from mature hepatocytes by using a low molecular weight compound (WO2017/119512).

However, except for the case of hepatocytes, there is no report about contribution of these low molecular weight inhibitors to the reprogramming of mature cells into stem/progenitor cells.

PRIOR ART DOCUMENTS

Patent Documents

Patent Document 1: WO2017/119512

Non-Patent Documents

Non-patent Document 1: Cell. 2014 Oct. 9; 159(2):428-39

Non-patent Document 2: Cell Metab. 2016 Apr. 12; 23(4): 622-634

Non-patent Document 3: Nat Commun. 2016 Jan. 6; 7:10080

Non-patent Document 4: Cell Stem Cell. 2016 Mar. 3; 18(3):410-21

Non-patent Document 5: Nat Biotechnol. 2014 December; 32(12):1223-30

Non-patent Document 6: EMBO J. 2013 Oct. 16; 32(20): 2708-21

Non-patent Document 7: Proc Natl Acad Sci USA. 2010 Aug. 10; 107(32): 14223-8

Non-patent Document 8: Cell Stem Cell. 2017 Jan. 5; 20(1):41-55

Non-patent Document 9: Cell Stem Cell. 2016 Oct. 6; 19(4):449-461

SUMMARY OF THE INVENTION

Problem to be Solved by the Invention

The objective of the present invention is to provide a method for efficiently reprogramming mature cells into stem/progenitor cells without genetic modification.

Means to Solve the Problem

In order to achieve the above-described objective, the inventors of the present invention have gone through intensive research, and as a result of which found that when mammalian mature cells (e.g., mature pancreatic exocrine cells) are cultured in the presence of a TGFβ-receptor inhibitor, a glycogen synthase kinase 3 (GSK3) inhibitor and a Rho kinase (ROCK) inhibitor, such pancreatic exocrine cells can be reprogrammed into cells that are proliferative and capable of differentiating into pancreatic endocrine cells. The inventors of the present invention have demonstrated that when the pancreatic stem/progenitor cells thus obtained from mature pancreatic exocrine cells are transplanted into diabetic model mice, they can be engrafted as mature pancreatic endocrine cells.

As a result of further studies based on these findings, the inventors of the present invention accomplished the present invention.

Thus, the present invention is as follows.

(1) A method starting from cells derived from a mammalian endodermal tissue or organ (except for the liver) to produce stem/progenitor cells thereof, which comprises bringing the cells derived from the endodermal tissue or organ into contact in vitro with a TGFβ-receptor inhibitor.

(2) The method according to (1) above, which further comprises bringing the cells derived from the endodermal tissue or organ into contact in vitro with a GSK3 inhibitor and/or a ROCK inhibitor.

(3) The method according to (1) above, which further comprises bringing the cells derived from the endodermal tissue or organ into contact in vitro with a GSK3 inhibitor and a ROCK inhibitor.

(4) The method according to any one of (1) to (3) above, wherein the endodermal tissue or organ is the digestive tract, lung, thyroid gland, pancreas, secretory gland, peritoneum, pleura, larynx, auditory tube, trachea, bronchus, urinary bladder, urethra or ureter.

(5) The method according to any one of (1) to (4) above, wherein the endodermal tissue or organ is the pancreas.

(6) The method according to (5) above, wherein the cells derived from the pancreas are pancreatic exocrine cells.

(7) The method according to (6) above, wherein the contact between the pancreatic exocrine cells and the TGFβ-receptor inhibitor is carried out by culturing the pancreatic exocrine cells in the presence of the inhibitor.

(8) The method according to (6) or (7) above, wherein the contact between the pancreatic exocrine cells and the GSK3 inhibitor and/or the ROCK inhibitor is carried out by culturing the pancreatic exocrine cells in the presence of the inhibitor(s).

(9) The method according to any one of (1) to (8) above, wherein the mammal is a human, a rat or a mouse.

(10) Pancreatic stem/progenitor cells derived from mammalian pancreatic exocrine cells, which have the following characteristics:

(a) having self-regeneration ability;
(b) being capable of differentiating into pancreatic endocrine cells; and
(c) expressing Pdx1 and Nkx6.1 but not expressing insulin.

(11) An inducer comprising a TGFβ-receptor inhibitor for inducing cells derived from a mammalian endodermal tissue or organ (except for the liver) into stem/progenitor cells thereof.

(12) The inducer according to (11) above, which further comprises a combination of a GSK3 inhibitor and/or a ROCK inhibitor.

(13) The inducer according to (11) above, which further comprises a combination of a GSK3 inhibitor and a ROCK inhibitor.

(14) The inducer according to any one of (11) to (13) above, wherein the endodermal tissue or organ is the digestive tract, lung, thyroid gland, pancreas, secretory gland, peritoneum, pleura, larynx, auditory tube, trachea, bronchus, urinary bladder, urethra or ureter.

(15) The inducer according to any one of (11) to (13) above, wherein the endodermal tissue or organ is the pancreas.

(16) The inducer according to (15) above, wherein the cells derived from the pancreas are pancreatic exocrine cells.

(17) The inducer according to any one of (11) to (16) above, wherein the mammal is a human, a rat or a mouse.

(18) The inducer according to any one of (11) to (17) above, which is used as an agent for maintaining or expanding the stem/progenitor cells obtained by the method according to any one of (1) to (9) above or the pancreatic stem/progenitor cells according to (10) above.

(19) A method for maintaining or expanding the stem/progenitor cells obtained by the method according to any one of (1) to (9) above or the pancreatic stem/progenitor cells according to (10) above, which comprises subculturing the stem/progenitor cells or the pancreatic stem/progenitor cells on a collagen- or Matrigel-coated culture vessel in the presence of a TGFβ-receptor inhibitor, a GSK3 inhibitor and a ROCK inhibitor.

(20) A method for inducing the stem/progenitor cells obtained by the method according to any one of (1) to (9) above or the pancreatic stem/progenitor cells according to (10) above into cells derived from a mammalian endodermal tissue or organ or into pancreatic exocrine cells, which comprises the step of culturing the stem/progenitor cells or the pancreatic stem/progenitor cells in the presence of a TGFβ-receptor inhibitor, a GSK3 inhibitor and a ROCK inhibitor.

(21) A method for assessing the metabolism of a test compound in the mammalian body, which comprises the steps of:

(i) bringing the test compound into contact with the stem/progenitor cells obtained by the method according to any one of (1) to (9) above, the pancreatic stem/progenitor cells according to (10) above or the cells obtained by the method according to (20) above; and
(ii) measuring the metabolism of the test compound in the cells.

(22) A screening method for secretion inducers of enzymes secreted from cells, which comprises the steps of:

(i) bringing a test compound into contact with the stem/progenitor cells obtained by the method according to any one of (1) to (9) above, the pancreatic stem/progenitor cells according to (10) above or the cells induced by the method according to (20) above; and
(ii) measuring the substance(s) secreted in the cells.

(23) A method for assessing the endodermal tissue or organ toxicity of a test compound on a mammal, which comprises the steps of:

(i) bringing the test compound into contact with the stem/progenitor cells obtained by the method according to any one of (1) to (9) above, the pancreatic stem/progenitor cells according to (10) above or the cells obtained by the method according to (20) above; and
(ii) measuring the presence or the absence, or the degree of damage in the cells contacted with the test compound.

(24) An agent for ameliorating endodermal tissue or organ damage, which comprises the stem/progenitor cells obtained by the method according to any one of (1) to (9) above, the pancreatic stem/progenitor cells according to (10) above or the cells obtained by the method according to (20) above.

(25) A method for ameliorating endodermal tissue or organ damage in a mammal, which comprises administering a mammal having the tissue or organ damage with an effective amount of the stem/progenitor cells obtained by the method according to any one of (1) to (9) above, the pancreatic stem/progenitor cells according to (10) above or the cells induced by the method according to (20) above.

(26) The stem/progenitor cells obtained by the method according to any one of (1) to (9) above, the pancreatic stem/progenitor cells according to (10) above or the cells obtained by the method according to (20) above for use as an agent for ameliorating endodermal tissue or organ damage.

Effects of the Invention

According to the present invention, pancreatic stem/progenitor cells having self-renewal ability and differentiation potency (bipotency) into pancreatic endocrine cells can safely and rapidly be induced from mature cells (e.g., pancreatic exocrine cells) without genetic modification.

DESCRIPTION OF EMBODIMENTS

1. Summary

Figure 1:
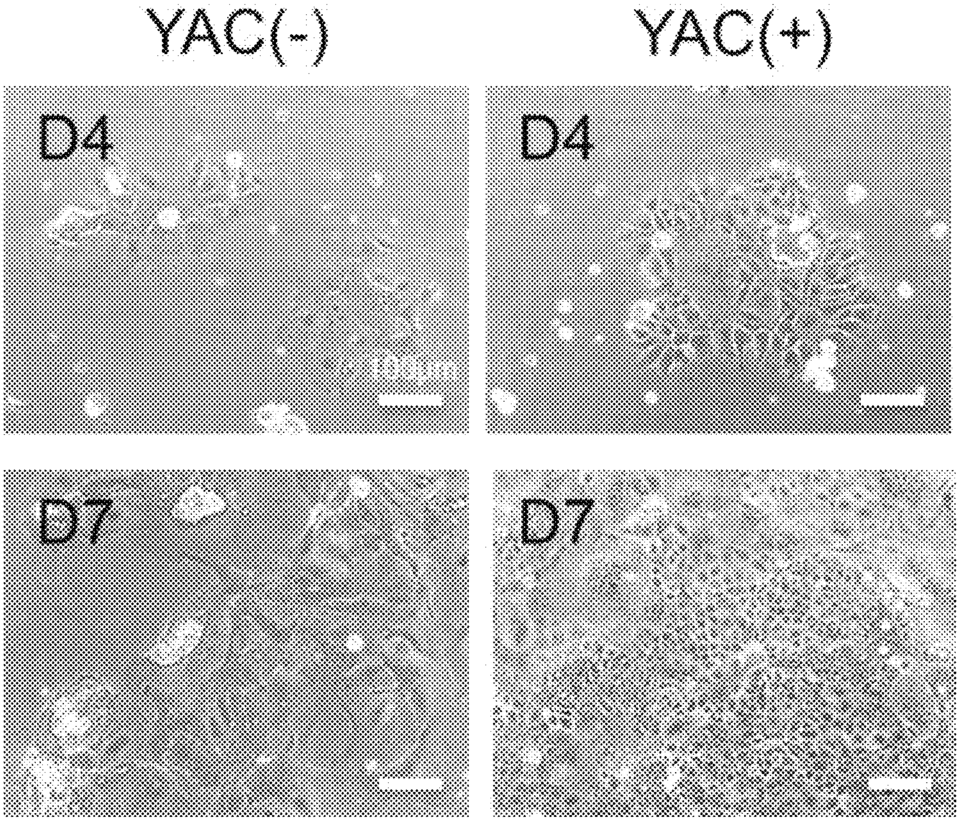
FIG. 1 shows changes in cell morphology upon induction of pancreatic progenitor cells.

The present invention provides a method starting from cells derived from a mammalian endodermal tissue or organ (except for the liver) to produce stem/progenitor cells thereof, which comprises bringing the cells derived from the endodermal tissue or organ into contact in vitro with a TGFβ-receptor inhibitor.

As described above, a method for producing hepatic stem/progenitor cells from mature hepatocytes by using a low molecular weight compound has been successfully provided by the inventors of the present invention (WO2017/119512). However, it is uncertain whether not only hepatocytes, but also other mature cells from endodermal organs or tissues can be reprogrammed into stem cells or progenitor cells (hereinafter referred to as "stem/progenitor cells").

When using cells from the pancreas as non-hepatocyte cells, the inventors of the present invention have succeeded in their reprogramming into pancreatic stem cells or pancreatic progenitor cells (hereinafter referred to as "pancreatic stem/progenitor cells") by the action of a low molecular weight compound.

As used herein, the term "stem cells" refers to cells that have self-renewal ability and pluripotency for differentiation into various cells, while the term "progenitor cells" refers to cells that develop from stem cells and are at an intermediate stage of differentiation into particular types of terminally differentiated cells constituting the body. These stem cells or progenitor cells are collectively referred herein to as "stem/progenitor cells" and are expressed as "pancreatic stem/progenitor cells" if the cells to be reprogrammed are pancreatic cells.

In the present invention, the "endoderm" is one of the three germ layers that arise during the development of metazoans, and embryologically constitutes the whole or part of the primitive gut wall during primitive gut formation (at the gastrula stage). The endoderm develops into the main part of the digestive tract and its accessory glands (liver, pancreas), thyroid gland, lung and other respiratory organs, etc.

In the present invention, the "endodermal tissue or organ" is exemplified by the digestive tract (esophagus, stomach, small intestine, large bowel), lung, pancreas, thyroid gland, parathyroid gland, larynx, trachea, bronchus, urinary bladder, urethra, prostate and so on (provided that the liver is excluded).

On the other hand, there are over 2,000 types of enzymes in the liver, and metabolic reactions are continuously carried out in the liver to chemically remake various substances. This is the reason why the liver is called "chemical factory in the body" and the liver greatly differs from any other endodermal tissues such as pancreatic beta cells having only the function of producing a single hormonal substance called insulin and a series of digestive system cells belonging to the endoderm. The liver shows the highest regeneration ability in the body, and when the liver and other endodermal tissues are compared for the degree of difficulty in their reprogramming, the endodermal tissues other than the liver are more significantly difficult to reprogram. Namely, once endoderm-derived cells have differentiated into mature cells, they will have characteristics peculiar to each organ in terms of proliferation ability, metabolic ability, humoral factor secretion ability, etc.; and hence it has been previously unknown whether the events found in mature hepatocytes are specific to mature hepatocytes or ubiquitous in endoderm-derived mature cells.

The inventors of the present invention have found that reprogramming from mature cells into stem/progenitor cells is also possible for endodermal tissues or organs other than the liver.

The present invention is characterized by bringing cells derived from a mammalian endodermal tissue or organ (except for the liver) into contact in vitro with a TGFβ-receptor inhibitor, but also comprises bringing these cells into contact with either or both of a glycogen synthase kinase 3 (GSK3) inhibitor and a Rho kinase (ROCK) inhibitor together with the TGFβ-receptor inhibitor. This allows, starting from mature cells derived from endodermal tissue or organ, to produce stem/progenitor cells of the endodermal tissue or organ. The method of the present invention is also referred to as "the reprogramming method of the present invention."

2. Induction of Stem/Progenitor Cells from Mature Cells

The present invention provides a method starting from cells derived from a mammalian endodermal tissue or organ (except for the liver) to produce stem/progenitor cells thereof, which comprises bringing the cells derived from the endodermal tissue or organ into contact in vitro with a TGFβ-receptor inhibitor.

To produce or induce pancreatic stem/progenitor cells from mature pancreatic exocrine cells, the present invention comprises bringing mammalian pancreatic exocrine cells into contact in vitro with low molecular weight signaling pathway inhibitors including a TGFβ-receptor inhibitor, a glycogen synthase kinase 3 (GSK3) inhibitor and a Rho kinase (ROCK) inhibitor.

The cells derived from the endodermal tissue or organ (except for the liver) (hereinafter also referred to as "mature cells") used as a starting material for the reprogramming method of the present invention are exemplified by digestive tract epithelial cells, alveolar epithelial cells, pancreatic parenchymal cells, thyroid gland follicular epithelial cells, urinary tract epithelial cells, prostate epithelial cells, etc. In the case of using pancreatic parenchymal cells as a starting material, pancreatic exocrine cells, pancreatic endocrine cells or the like can be used. "Pancreatic exocrine cells" are classified into acinar cells and pancreatic duct cells, either or both of which are deemed to serve as a starting source for pancreatic stem/progenitor cells. Likewise, "pancreatic endocrine cells" are classified into α cells, β cells, δ cells, ε cells and PP cells, any or all of which are deemed to serve as a starting source for pancreatic stem/progenitor cells.

The cells used for the reprogramming method of the present invention may be provided from any source, and examples include mammalian (e.g., human, rat, mouse, guinea pig, rabbit, sheep, horse, pig, bovine, monkey or the like, preferably human, rat or mouse) embryonic stem cells (ES cells) or pluripotent stem cells such as iPS cells.

However, considering that the main problem of the present invention is to safely and rapidly provide stem/progenitor cells without genetic modification, for example in the case of using pancreatic exocrine cells, those isolated/purified from a pancreas removed from a mammal are favorably used.

For example, in a case of a rat, a pancreas removed from a 10- to 20-week-old adult rat is preferably used, although a pancreas derived from a juvenile rat less than 2-month-old may also be used. In a case of a human, a pancreas may be obtained by biopsy or surgical operation. For example, pancreatic parenchyma, digestive tract epithelium, alveolar epithelium, prostatic epithelium and others may all be taken by biopsy. In the case of surgical operation, it is possible to use a pancreatic tissue piece sectioned from an adult or a pancreas sectioned from an aborted fetus. Alternatively, cells obtained by cryopreserving these isolated/purified pancreatic exocrine cells removed from the pancreas (cryopreserved pancreatic exocrine cells) may also be used.

For purification of cells derived from a mammalian endodermal tissue or organ, the tissue is isolated and enzymatically treated, followed by filtration, centrifugation, etc., to purify the cells.

For purification of pancreatic exocrine cells from a mammalian pancreas or a tissue piece thereof, the pancreatic tissue is isolated and digested with collagenase, followed by filtration, centrifugation, etc., to remove Langerhans' islets, non-parenchymal cells and cell debris, thereby purifying pancreatic exocrine cells.

The mature cells (e.g., pancreatic exocrine cells) prepared as described above are brought into contact in vitro with one or more low molecular weight signaling pathway inhibitors including a TGFβ-receptor inhibitor.

The TGFβ-receptor inhibitor used for the present invention may be any inhibitor as long as it inhibits the function of the transforming growth factor (TGF) β-receptor, where examples include 2-(5-benzo[1,3]dioxole-4-yl-2-tert-butyl-1H-imidazol-4-yl)-6-methylpyridine, 3-(6-methylpyridine-2-yl)-4-(4-quinolyl)-1-phenylthiocarbamoyl-1H-pyrazole (A-83-01), 2-(5-chloro-2-fluorophenyl)pteridine-4-yl)pyridine-4-ylamine (SD-208), 3-(pyridine-2-yl)-4-(4-quinonyl)]-1H-pyrazole, 2-(3-(6-methylpyridine-2-yl)-1H-pyrazole-4-yl)-1,5-naphthyridine (all from Merck) and SB431542 (Sigma Aldrich). A preferable example includes A-83-01. The TGFβ-receptor inhibitor also comprises a TGFβ-receptor antagonist.

The TGFβ-receptor inhibitor may be one type of compound or a combination of two or more types compounds.

Examples of a low molecular weight signaling pathway inhibitor other than the TGFβ-receptor inhibitor preferably include a GSK3 inhibitor and a ROCK inhibitor.

The GSK3 inhibitor used for the present invention may be any inhibitor as long as it inhibits the function of glycogen synthase kinase (GSK) 3, where examples include SB216763 (Selleck), CHIR98014, CHIR99021 (all from Axon medchem), SB415286 (Tocris Bioscience), and Kenpaullone (Cosmo Bio). A preferable example includes CHIR99021.

The GSK3 inhibitor may be one type of compound or a combination of two or more types compounds.

The ROCK inhibitor used for the present invention may be any inhibitor as long as it inhibits the function of Rho-binding kinase. Examples of the ROCK inhibitor include GSK269962A (Axon medchem), Fasudil hydrochloride (Tocris Bioscience), Y-27632 and H-1152 (all from Wako Pure Chemical). A preferable example includes Y-27632.

The ROCK inhibitor may be one type of compound or a combination of two or more types compounds.

When the GSK3 inhibitor and the ROCK inhibitor are used alone or in combination and brought together with the TGFβ-receptor inhibitor into contact with the mature cells (e.g., pancreatic exocrine cells), the efficiency of inducing stem/progenitor cells (also referred to as "reprogramming efficiency") is significantly increased as compared to the case where only the TGFβ-receptor inhibitor is brought into contact with the mature cells. Therefore, according to the reprogramming method of the present invention, the GSK3 inhibitor and/or the ROCK inhibitor, in addition to the TGFβ-receptor inhibitor, is preferably brought into contact with the mature cells (e.g., pancreatic exocrine cells).

In the present invention, combinations of the TGFβ-receptor inhibitor and the GSK3 inhibitor and/or the ROCK inhibitor are shown below.

(a) A-83-01 (A) as the TGFβ-receptor inhibitor in combination with CHIR99021 (C) as the GSK3 inhibitor (AC).

(b) A-83-01 (A) as the TGFβ-receptor inhibitor in combination with Y-27632 (Y) as the ROCK inhibitor (YA).

(c) A-83-01 (A) as the TGFβ-receptor inhibitor in combination with CHIR99021 (C) as the GSK3 inhibitor and Y-27632 (Y) as the ROCK inhibitor (YAC).

When the GSK3 inhibitor and the ROCK inhibitor are used in combination with the TGFβ-receptor inhibitor, the difference in the reprogramming effect is small from that obtained with a combination of the TGFβ-receptor inhibitor and the GSK3 inhibitor, but the former gives better proliferation ability of the resulting stem/progenitor cells than the latter. Therefore, in an embodiment of the present invention, it is further preferred that a combination of the TGFβ-receptor inhibitor, the GSK3 inhibitor and the ROCK inhibitor is brought into contact with the mature cells (e.g., pancreatic exocrine cells).

According to the reprogramming method of the present invention, a low molecular weight signaling pathway inhibitor other than the GSK3 inhibitor and the ROCK inhibitor may also be combined with the TGFβ-receptor inhibitor. An example of such an inhibitor includes, but not limited to, a MEK inhibitor. The MEK inhibitor is not particularly limited and any inhibitor may be used as long as it inhibits the function of MEK (MAP kinase-ERK kinase), where examples include AZD6244, CI-1040 (PD184352), PD0325901, RDEA119 (BAY86-9766), SL327, U0126-EtOH (all from Selleck), PD98059, U0124 and U0125 (all from Cosmo Bio).

According to the reprogramming method of the present invention, contact between mature cells (e.g., pancreatic exocrine cells) and the low molecular weight signaling pathway inhibitors including the TGFβ-receptor inhibitor can be carried out by culturing the mature cells in the presence of these inhibitors. Specifically, these inhibitors are added to a medium at an effective concentration to carry out the culturing. As this medium, a medium widely used for culturing animal cells may be utilized as a basal medium. A commercially available basal medium may also be employed, where examples include, but not particularly limited to, a minimum essential medium (MEM), a Dulbecco's modified minimum essential medium (DMEM), a RPMI1640 medium, a 199 medium, a Ham's F12 medium and a William's E medium, which may be used alone or two or more types of them may be used in combination.

Examples of additives to the medium include various amino acids (for example, L-glutamine, L-proline, etc.), various inorganic salts (salt of selenious acid, $NaHCO_3$, etc.), various vitamins (nicotinamide, ascorbic acid derivative, etc.), various antibiotics (for example, penicillin, streptomycin, etc.), an antimycotic agent (for example, amphotericin, etc.), and buffers (HEPES, etc.).

In addition, a 5-20% serum (FBS, etc.) may be added to the medium, or the medium may be a serum-free medium. In a case of a serum-free medium, a serum substitute (BSA, HAS, KSR, etc.) may be added. In general, a factor such as a growth factor, cytokine or hormone is further added. Examples of such factors include, but not limited to, epidermal growth factor (EGF), insulin, transferrin, hydrocortisone 21-hemisuccinate or a salt thereof and dexamethasone (Dex).

The concentration of the TGFβ-receptor inhibitor added to the medium may suitably be selected, for example, in a range of 0.01-10 μM, and preferably 0.1-1 μM.

The concentration of the GSK3 inhibitor added to the medium may suitably be selected, for example, in a range of 0.01-100 μM, and preferably 1-10 μM.

The concentration of the ROCK inhibitor added to the medium may suitably be selected, for example, in a range of 0.0001-500 μM, and preferably 1-50 μM.

When these inhibitors are water-insoluble or poorly water-soluble compounds, they may be dissolved in a small amount of a low-toxicity organic solvent (for example, DMSO, etc.), and then the resultant can be added to a medium to give the above-described final concentration.

The culture vessel used for this culture is not particularly limited as long as it is suitable for adhesion culture, where examples include a dish, a petri dish, a tissue culture dish, a multidish, a microplate, a microwell plate, a multiplate, a multiwell plate, a chamber slide, a Schale, a tube, a tray, and a culture bag. For floating cell culture, the culture vessel used may have its surface treated to avoid cell adhesion. Alternatively, in the case of adhesion culture, the culture vessel used may have its inner surface coated with a cell supporting substrate for the purpose of enhancing adhesiveness with the cells. Examples of such a cell supporting substrate include collagen, gelatin, Matrigel, poly-L-lysine, laminin and fibronectin, and preferably collagen and Matrigel.

The mature cells can be seeded onto a culture vessel at a cell density of $10^2$-$10^6$ cells/cm$^2$, and preferably $10^3$-$10^5$ cells/cm$^2$.

In the case of pancreatic exocrine cells, they can also be seeded onto a culture vessel at a cell density of $10^2$-$10^6$ cells/cm$^2$, and preferably $10^3$-$10^5$ cells/cm$^2$. Culture can take place in a $CO_2$ incubator, in an atmosphere at a $CO_2$ concentration of 1-10%, preferably 2-5% and more preferably about 5%, at 30-40° C., preferably 35-37.5° C. and more preferably about 37° C. The culture period may be, for example, 1-4 weeks, and preferably 1-3 weeks. The medium is freshly exchanged every 1-3 days.

In this manner, the mature cells (pancreatic exocrine cells) are brought into contact with the TGFβ-receptor inhibitor, and optionally the GSK3 inhibitor and/or the ROCK inhibitor so as to reprogram the mature cells into stem/progenitor cells. For example, once primary mouse mature pancreatic exocrine cells have been cultured with A-83-01 as the TGFβ-receptor inhibitor (A) in combination (YAC) with CHIR99021 as the GSK3 inhibitor (C) and Y-27632 as the ROCK inhibitor (Y), they will proliferate by about 3000 times by 30 days of culture and show a significant increase as compared to culture in the absence of YAC.

As used herein, the term "pancreatic stem/progenitor cells" (hereinafter also referred to as "PSCs") refers to stem cells or progenitor cells which have (a) self-regeneration ability and (b) the ability to differentiate into pancreatic endocrine cells (e.g., cells constituting Langerhans' islets) or pancreatic exocrine cells.

The pancreatic stem/progenitor cells (PSCs) also include pancreatoblasts from a fetal pancreas.

According to one preferable embodiment, in addition to the features (a) and (b) above, PSCs obtained by the reprogramming method of the present invention (c) express master factors Pdx1 and Nkx6.1, and also express Gata4, Hest, Sox9, Foxa2, CK19, CD133 and so on. However, PSCs obtained by the reprogramming method of the present invention do not express Lgr5 which is expressed in other known PSCs. Thus, PSCs of the present invention are regarded as novel PSCs.

PSCs of the present invention further have one or more of the following features.

(d) the apparent growth rate does not slow down for at least 10 passages, preferably 20 passages or more of subculture.

(e) differentiation potency into pancreatic endocrine cells is retained for at least 10 passages, preferably 20 passages or more of subculture.

(f) nuclear cytoplasmic (N/C) ratio is higher than that of pancreatic exocrine cells.

(g) expressions of one or more PSC marker genes selected from Pdx1 and Nkx6.1 are increased compared to pancreatic exocrine cells.

(h) expressions of one or more proteins selected from Pdx1 and Nkx6.1 are increased compared to pancreatic exocrine cells.

According to a preferable embodiment, PSCs of the present invention have all of the above-described features (d)-(h).

As described above, when brought into contact with a TGFβ-receptor inhibitor, a GSK3 inhibitor and/or a ROCK inhibitor, mature cells (e.g., pancreatic exocrine cells) can be induced into stem/progenitor cells (e.g., pancreatic exocrine cells can be induced into PSCs).

Therefore, the present invention provides a method for inducing cells derived from a mammalian endodermal tissue or organ (except for the liver) into stem/progenitor cells thereof, which comprises bringing the cells derived from the endodermal tissue or organ into contact in vitro with a TGFβ-receptor inhibitor or with a combination of a TGFβ-receptor inhibitor, a GSK3 inhibitor and/or a ROCK inhibitor.

Particularly in the case of inducing pancreatic exocrine cells into PSCs, the present invention provides a method for inducing pancreatic exocrine cells into PSCs by bringing the pancreatic exocrine cells into contact with a TGFβ-receptor inhibitor, a GSK3 inhibitor and/or a ROCK inhibitor. The present invention also provides a PSC inducer comprising a TGFβ-receptor inhibitor for inducing pancreatic exocrine cells into PSCs. The PSC inducer of the present invention preferably comprises a combination of a TGFβ-receptor inhibitor, a GSK3 inhibitor and/or a ROCK inhibitor, more preferably comprises a combination of a TGFβ-receptor inhibitor, a GSK3 inhibitor and a ROCK inhibitor.

While the TGFβ-receptor inhibitor, the GSK3 inhibitor and the ROCK inhibitor can directly be used as a PSC inducer, they may also be made into a liquid agent by dissolving them in a suitable solvent. Alternatively, these inhibitors can be made into a kit by combining with the above-described medium for inducing PSCs from pancreatic exocrine cells.

3. Maintenance and Expansion of Stem/Progenitor Cells

The stem/progenitor cells of the present invention obtained as described above can be efficiently maintained or expanded by being subcultured on a collagen- or Matrigel-coated culture vessel in the presence of a TGFβ-receptor inhibitor, a GSK3 inhibitor and a ROCK inhibitor.

As the culture vessel, a culture vessel similar to one used for inducing mature cells into stem/progenitor cells can be used.

In the case of using pancreatic exocrine cells, PSCs obtained by the method of the present invention can be efficiently maintained or expanded by being subcultured on a collagen- or Matrigel-coated culture vessel in the presence of a TGFβ-receptor inhibitor, a GSK3 inhibitor and a ROCK inhibitor.

As the culture vessel, a culture vessel similar to one used for inducing pancreatic exocrine cells into PSCs can be used.

Once the primary PSCs obtained as described above have reach 70-100% confluency, they are seeded onto this collagen- or Matrigel-coated culture vessel at a density of $10^3$-$10^5$ cells/cm$^2$. As the medium, the medium described for induction culture of PSCs can similarly be used. The concentrations of the TGFβ-receptor inhibitor, the GSK3 inhibitor and the ROCK inhibitor added can also suitably be selected from the concentration ranges described above for induction culture of PSCs. The culture temperature and the $CO_2$ concentration also follow the conditions for induction culture of PSCs. Once 70-100% confluency has been reached, the cells are treated with trypsin to be dissociated, and subcultured. Stable PSCs can be obtained after about 5-8 passages of subculture. After 10 passages or more of subculture, cloning can be conducted by a routine procedure.

As described above, the TGFβ-receptor inhibitor, the GSK3 inhibitor and the ROCK inhibitor are added to the medium not only for induction culture but also for maintenance or expansion culture of stem/progenitor cells (e.g., PSCs). Thus, the present invention also provides an agent for maintaining or expanding stem/progenitor cells (e.g., PSCs), which comprises a TGFβ-receptor inhibitor, a GSK3 inhibitor and a ROCK inhibitor.

4. Differentiation from Stem/Progenitor Cells into Mature Cells

Induction of differentiation from stem/progenitor cells into mature cells may be accomplished, for example, by floating culture in SHM (Small hepatocyte medium) supplemented with YAC on an ultra-low adsorption culture dish for 7 days. Alternatively, it is also possible to use, e.g., a method for culture in a culture solution supplemented with Phorbol 12,13-dibutyrate, LDN193189, Keratinocyte Growth Factor, SANT1, Retinoic Acid, XXI, Betacellulin and so on (Cell. 2014 Oct. 9; 159(2):428-39).

Induction of differentiation from PSCs into pancreatic endocrine cells may also be accomplished in the same manner as described above. Alternatively, it is also possible to use, e.g., a method for culture in a culture solution supplemented with Phorbol 12,13-dibutyrate, LDN193189, Keratinocyte Growth Factor, SANT1, Retinoic Acid, XXI, Betacellulin and so on (Cell. 2014 Oct. 9; 159(2):428-39).

When PSCs of the present invention are induced to differentiate, the resulting pancreatic exocrine cells have the insulin-producing function typical of mature pancreatic endocrine cells, and C-peptide secretion reflecting insulin secretion is also detected. Moreover, increases in mRNA levels are observed for Ngn3 and glucose transporter (GLUT2) which are master transcription factors in pancreatic endocrine cells. Namely, PSCs of the present invention are capable of differentiating into functional pancreatic endocrine cells.

5. Application of the Stem/Progenitor Cells of the Present Invention

The mature cells redifferentiated from the stem/progenitor cells of the present invention as described in Item 4 above can be utilized, for example, for assessing metabolism and cell or tissue toxicity of a test compound.

Conventionally, animal models or the like have been used for the assessment of metabolism and toxicity of a test compound, but there are problems like limitation in the number of the test compounds that can be assessed at one time and assessments obtained with animal models or the like being unable to directly be applied to human. Therefore, an assessment method using a human cancer cell line or a primary culture of normal human cells has been employed. However, assessment obtained with the human cancer cell line may possibly be inapplicable to normal human cells. In addition, the primary cultures of normal human cells are associated with problems in terms of stable supply and cost. Moreover, cell lines obtained by immortalizing primary cultures of normal human cells are shown to have lower activity as compared to those not immortalized. These problems may be solved by utilizing cells produced according to the method of the present invention.

Thus, the present invention provides a method for assessing the metabolism of a test compound in the mammalian body, which comprises the steps of: bringing the test compound into contact with the stem/progenitor cells obtained by the method of the present invention, the pancreatic stem/progenitor cells of the present invention or the cells obtained by the induction method of the present invention; and measuring the metabolism of the test compound in the cells.

Thus, in the case of using pancreatic exocrine cells in the method of the present invention, a test compound is brought into contact with pancreatic exocrine cells produced by the method of the present invention, followed by measuring the metabolism of the test compound contacted with the pancreatic exocrine cells.

The test compound used with the present invention is not particularly limited. Examples include, but not limited to, a xenobiotic substance, a natural compound, an organic compound, an inorganic compound, a protein, a single compound such as a peptide, an expression product from a compound library or a gene library, a cell extract, a cell culture supernatant, a fermentative microbial product, a marine organism extract and a plant extract.

Examples of the xenobiotic substance include, but not limited to, candidate compounds for drugs and food, existing drugs and food, and the xenobiotic substance intended in the present invention comprises any substance as long as it is a foreign matter to the living body. More specific examples include Rifampin, Dexamethasone, Phenobarbital, Ciglirazone, Phenytoin, Efavirenz, Simvastatin, β-Naphthoflavone, Omeprazole, Clotrimazole and 3-Methylcholanthrene.

Contact between mature cells (e.g., pancreatic exocrine cells) and a test compound is usually carried out by adding the test compound to a medium or a culture solution, but it is not limited thereto. If the test compound is a protein or the like, a DNA vector expressing said protein may be introduced into the cells to make contact therewith.

The metabolism of the test compound can be measured by a method well known to those skilled in the art. For example, the test compound is judged to have been metabolized if a metabolite of the test compound is detected.

For example, the test compound is also judged to have been metabolized if expression of an enzyme gene such as insulin is induced or activity of such enzyme is increased upon contact with the test compound.

In the case of tissues or organs other than the pancreas, the test compound may also be judged to have been metabolized on the basis of the expression of a gene present in such tissue or organ.

The present invention also provides a screening method for secretion inducers of enzymes secreted from cells, which comprises the steps of: bringing a test compound into contact with the stem/progenitor cells obtained by the method of the present invention, the pancreatic stem/progenitor cells of the present invention or the cells induced by the induction method of the present invention; and measuring the substance(s) secreted in the cells.

For example, screening for secretion modulators can be made on the basis of whether upon contact with a test substance, pancreatic stem/progenitor cells or induced pancreatic cells are induced to secret each enzyme to be secreted therefrom.

The present invention also provides a method for assessing the endodermal tissue or organ toxicity of a test compound on a mammal. This method comprises the steps of: bringing the test compound into contact with the stem/progenitor cells obtained by the method of the present invention, the pancreatic stem/progenitor cells of the present invention or the cells induced by the induction method of the present invention; and measuring the presence or the absence, or the degree of damage in the cells contacted with the test compound.

In the case of assessing the pancreatic toxicity of a test compound in the present invention, the test compound is brought into contact with pancreatic exocrine cells produced by the method of the present invention, followed by measuring the degree of damage in the pancreatic exocrine cells contacted with the test compound. The degree of damage may be measured, for example, on the basis of the viability of pancreatic exocrine cells or pancreatic damage markers.

For example, a test compound is judged to have pancreatic toxicity if the viability of pancreatic exocrine cells is decreased upon adding the test compound to the culture solution of the pancreatic exocrine cells, whereas a test compound is judged to have no pancreatic toxicity when there is no significant change in the viability.

Here, a compound whose presence or absence of pancreatic toxicity is already known can be used as a control so as to assess whether or not a test compound has pancreatic toxicity in a more accurate way.

Further, the present invention provides an agent for ameliorating endodermal tissue or organ damage, which comprises the stein/progenitor cells obtained by the method of the present invention, the pancreatic stein/progenitor cells of the present invention or the cells induced by the induction method of the present invention. Furthermore, the present invention provides the above method, which comprises administering a mammal having endodermal tissue or organ damage with an effective amount of the stein/progenitor cells obtained by the method of the present invention, the pancreatic stem/progenitor cells of the present invention or the cells induced by the induction method of the present invention.

For example, to ameliorate pancreatic damage, PSCs of the present invention can be transplanted into an immunodeficient mouse with chronic pancreatic damage so as to exert pancreatic regeneration ability comparative to transplantation of primary mature pancreatic exocrine cells. Thus, the present invention also provides an agent for ameliorating pancreatic damage, which comprises PSCs of the present invention.

If necessary, PSCs of the present invention may be purified before use by flow cytometry using an antibody against a surface antigen marker. PSCs can be suspended in a suitable isotonic buffer (for example, PBS) to be formulated. If necessary, a pharmaceutically acceptable additive can further be contained. Although the PSC suspension may differ depending on the type of pancreatic disease, the severity of pancreatic damage or the like, for example, $10^8$-$10^{11}$ cells can be transplanted in a case of an adult.

Hereinafter, the present invention will be described more specifically by way of examples, although the present invention should not be limited to these examples in any way.

EXAMPLES

1. Experimental Procedures

Establishment of Pancreatic Progenitor Cells

Mouse or rat pancreatic exocrine cells were treated with collagenase and isolated in accordance with known techniques (Reichert et al. Cold Spring Harb Protoc. 2015 Jun. 1; 2015(6):558-61). Dithizone (DTZ) staining was conducted to confirm the absence of insulin-secreting cells among the isolated cells. The isolated pancreatic exocrine cells were plated on a type I collagen-coated culture dish using Small hepatocyte medium (SHM) supplemented with three types of low molecular weight compounds (Y-27632 [10 μM], A-83-01 [0.5 μM], CHIR99021 [3 μM]; hereinafter referred to as YAC).

SHM medium: DMEM/F12 (472.7 mL) supplemented with the additives shown below (Katsuda et al. Bio Protoc. 2018 Jan. 20; 8(2)):

- 2 M HEPES, 1.25 mL
- 30 g/L L-proline, 500 μL
- 100× antibiotic/antimycotic, 5 ml
- 5 N NaOH, 250 μL (for adjustment to pH 7.5)
- 5% BSA, 5 mL
- 10 μg/mL EGF, 500 μL
- 100×ITS-X, 5 mL
- $10^{-4}$ M dexamethasone, 500 μL
- 1 M nicotinamide, 5 mL
- 100 mM Asc2P, 5 mL Subculture of PSCs On the 14th day of primary culture, the cells cultured in the presence of YAC were collected by treatment with trypsin, and then seeded at $9\times10^3$ cells/cm$^2$ in SHM supplemented with YAC. The mouse cells were cultured on a type I collagen-coated culture dish, while the rat cells were cultured on a Matrigel-coated culture dish. CELLBANKER® 1 (TaKaRa Shuzo, Otsu) was used to prepare cryopreserved stocks. After at least 10 passages of subculture, PSCs were cloned using a BD FACSAria II cell sorter.

Low-Speed Imaging at Low Cell Density

The primary pancreatic exocrine cells were seeded onto a collagen-coated 35-mm plate (IWAKI) in the presence or the absence of YAC at $1\times10^2$ cells/cm$^2$. On the first day, the medium was exchanged. After the second medium exchange, BZ9000 All-in-One Fluorescence Microscope (Keyence, Osaka) was used to perform low-speed imaging. Phase difference images were taken every 30 minutes for 300 times from Day 2 to Day 6, and movies were made for every analytical field. Next, individual cells were traced throughout the imaging period to determine the final cell count originating from the cells of interest. Additionally, the total number of apoptotic cells originating from the individual cells was also counted to quantitate apoptotic frequency as total apoptotic cells/original total cell count (counted at the beginning of low-speed imaging).

Quantitative RT-PCR

Total RNA was isolated from the pancreatic exocrine cells and PSC cells using miRNeasy Mini Kit (QIAGEN). Reverse transcription reaction was carried out using High-Capacity cDNA Reverse Transcription Kit (Life Technologies) following the manufacturer's guideline. The resulting cDNA was used as a template to perform PCR with Platinum SYBR Green qPCR SuperMix UDG (Invitrogen). The expression level of the target gene was normalized with β-actin as the endogenous control.

Immunocytochemistry and Immunohistochemistry

The cells were fixed with 4% paraformaldehyde for 15 minutes. The resultant was incubated with a blocking solution (Blocking One) (Nacalai Tesque, Kyoto) at 4° C. for 30 minutes, and then the cells were incubated with primary antibody at room temperature for an hour or at 4° C. overnight. Then, Alexa Fluor 488- or Alexa Fluor 594-labeled secondary antibody (Life Technologies) was used to detect the primary antibody. The nuclei were co-stained with Hoechst 33342 (Dojindo).

The tissue sample was fixed with formalin and paraffin-embedded. After dewaxing and rehydration, the specimen was boiled in a 1/200 diluted ImmunoSaver (Nisshin EM, Tokyo) at 98° C. for 45 minutes to retrieve the heat-induced epitope. Then, the specimen was treated with 0.1% Triton-X 100 for membrane permeabilization. Following treatment with a blocking reagent (Nacalai Tesque) at 4° C. for 30 minutes, the specimen was incubated with a primary antibody at room temperature for an hour. These sections were stained using ImmPRESS IgG-peroxidase kit (Vector Labs) and metal-enhanced DAB substrate kit (Life Technologies) following the manufacturers' instructions. After counter-staining with hematoxylin, the specimen was dehydrated and mounted.

Induction from PSCs into Pancreatic Endocrine Cells

The cells were suspended in 5% FBS-containing SHM+YAC (cell density: $1\times10^4$ to $1\times10^6$ cells/cm$^2$) and cultured on an ultra-low adsorption culture dish for 7 days. The medium was exchanged on the fourth day.

2. Results

1) Establishment of Pancreatic Progenitor Cells

A medium containing pancreatic exocrine cells was supplemented with YAC to thereby establish small epithelial cells having high proliferation ability as shown in FIG. 1. These cells were able to be subcultured for over 20 passages and were able to be grown in single cell culture. Moreover, these cells are capable of differentiating into endocrine system cells having the ability to synthesize insulin, and are therefore regarded as having characteristics as pancreatic progenitor cells.

2) Properties of Induced Pancreatic Progenitor Cells

Figure 2:
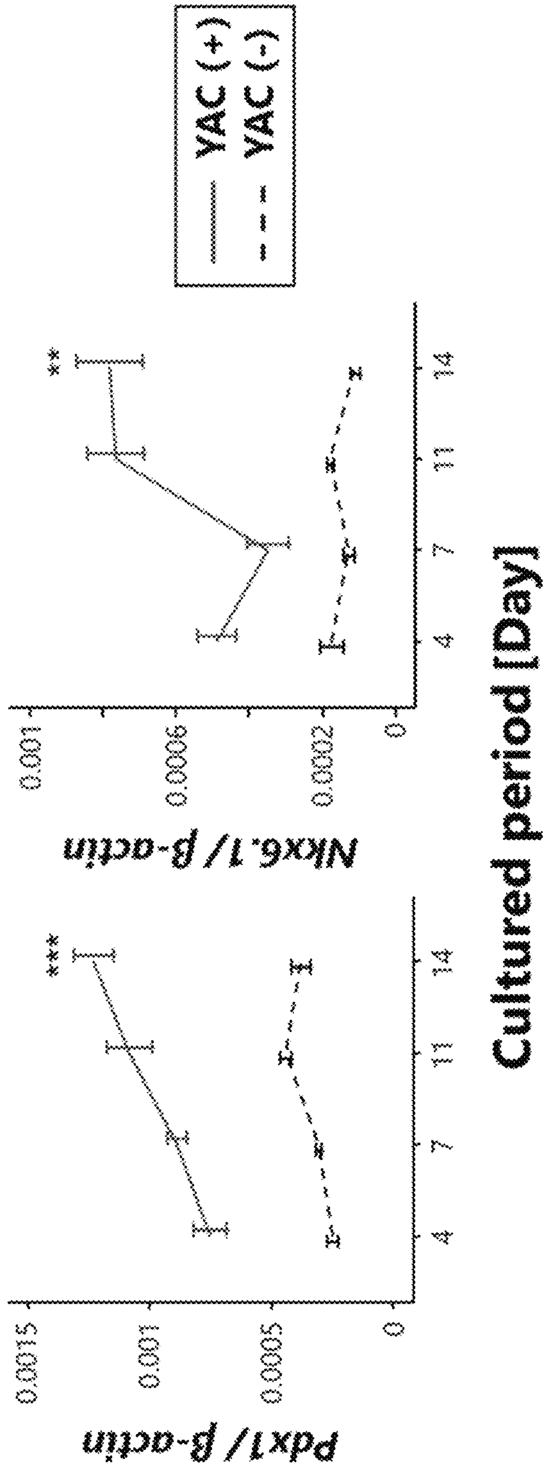
FIG. 2 shows changes in mRNA expression of pancreatic progenitor cell markers (mouse) upon induction of pancreatic progenitor cells.
Figure 3:
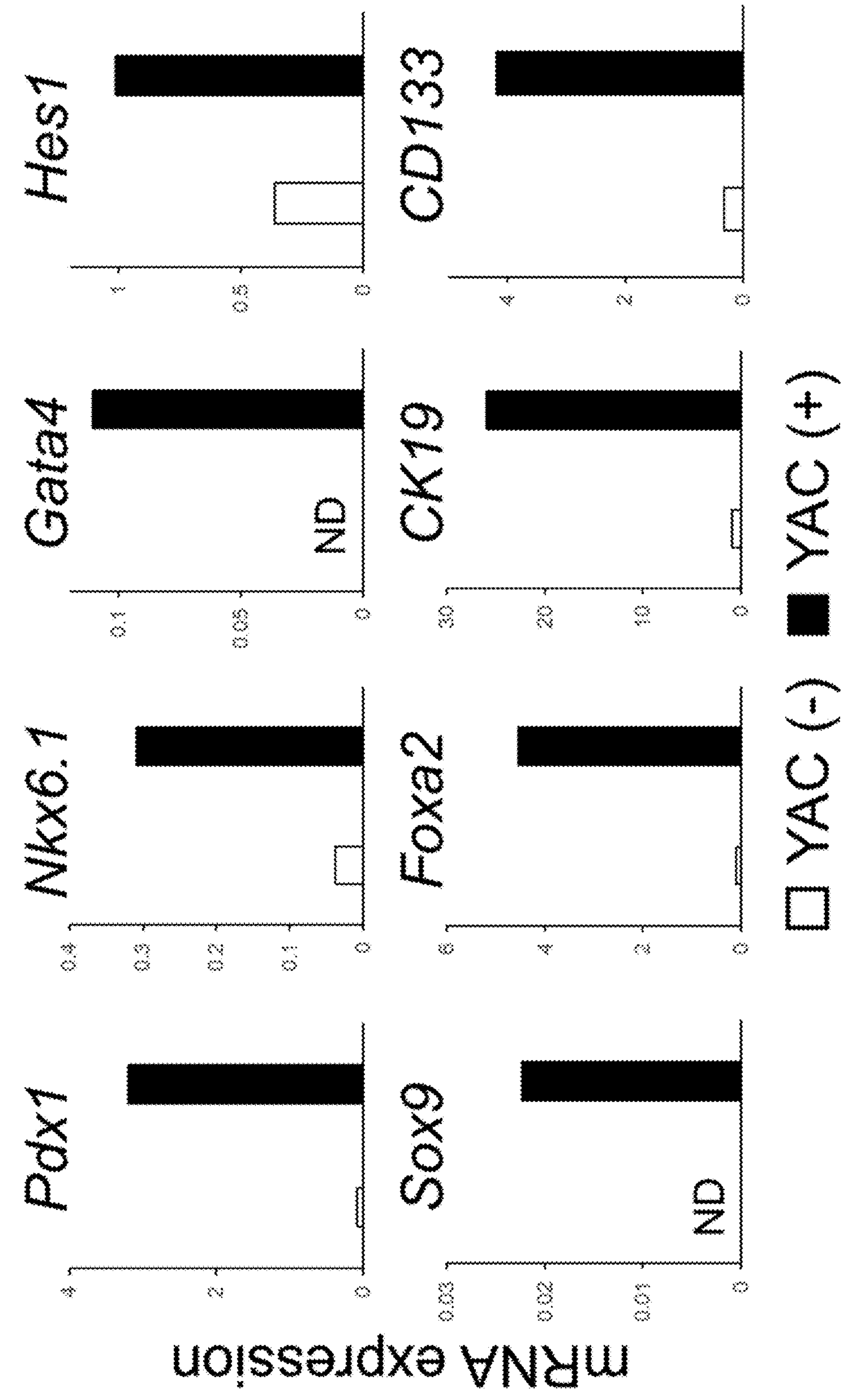
FIG. 3 shows mRNA expression of pancreatic progenitor cell markers (rat) after the first passage of subculture.

The establish cells were found to express stem cell markers including Pdx1 and Nkx6.1 which are master transcription factors in pancreatic progenitor cells, as shown in FIGS. 2 and 3.

Figure 4:
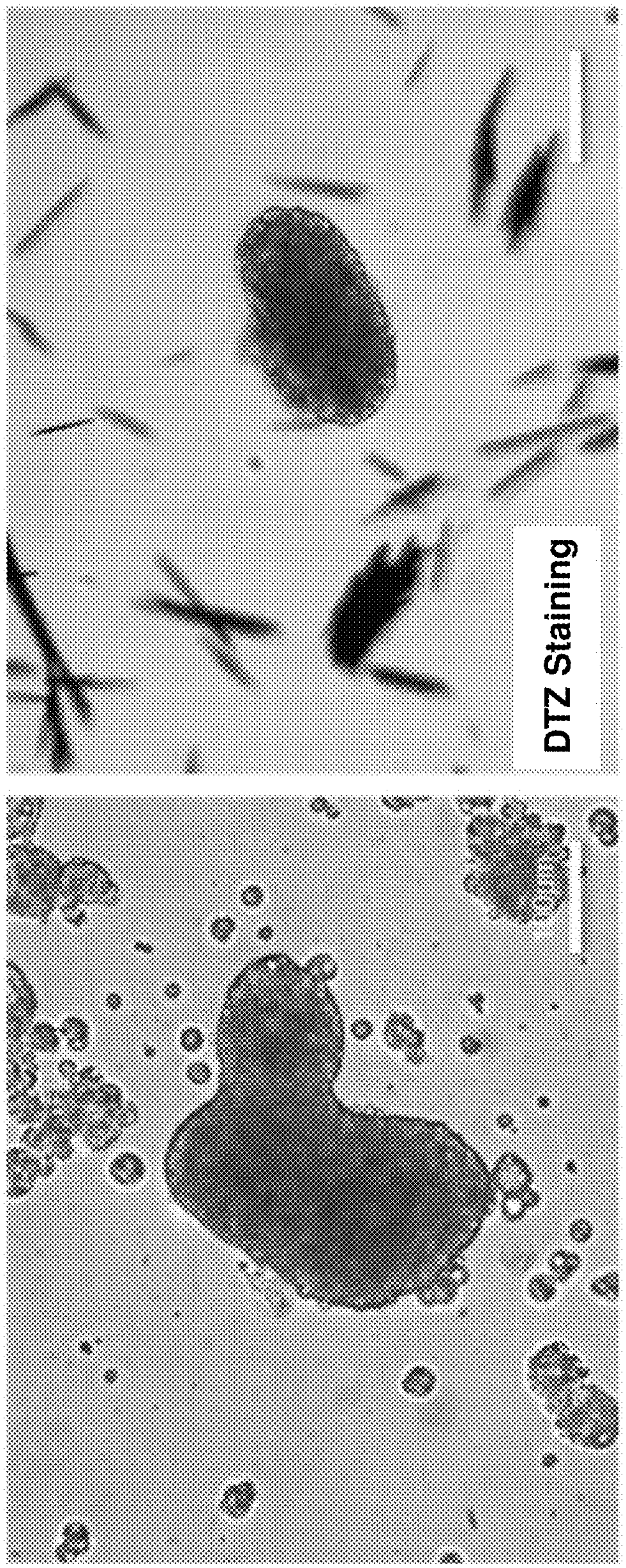
FIG. 4 shows clusters of insulin-secreting cells.
Figure 5:
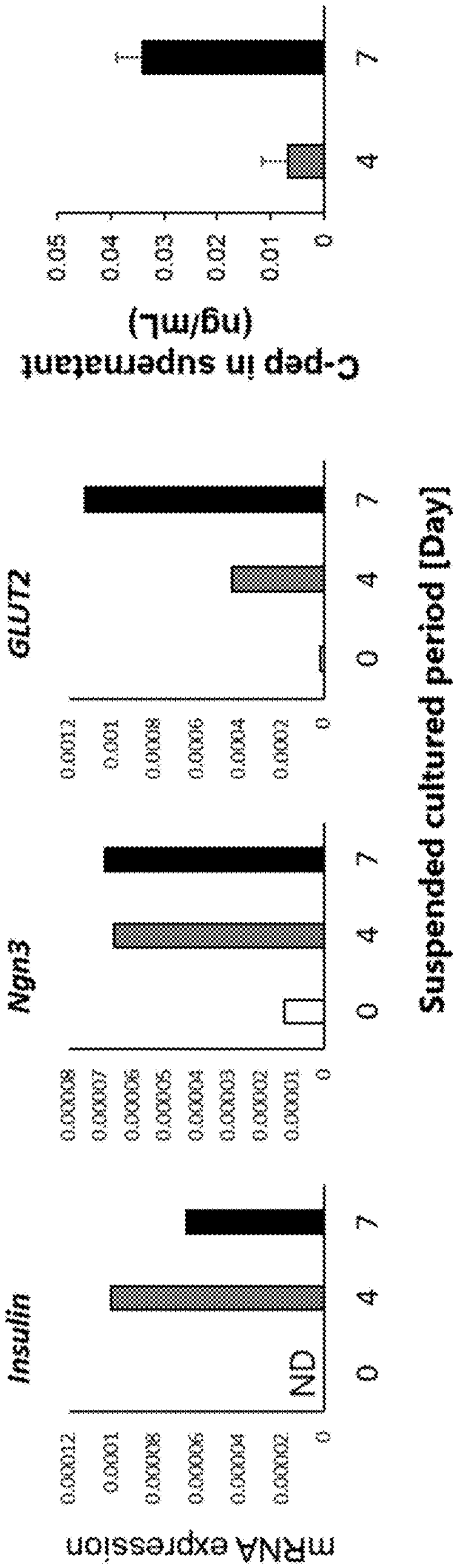
FIG. 5 shows mRNA expression of β cell marker molecules and C-peptide secretion in clusters of insulin-secreting cells.

3) Induction of Differentiation from Pancreatic Progenitor Cells into Insulin-Producing Cells Upon floating culture for 7 days using SHM medium supplemented with YAC on an ultra-low adsorption culture dish, the established pancreatic progenitor cells were found to proliferate while gathering in a cluster as shown in FIG. 4. This cluster was positive for DTZ staining, and stainability for insulin was detected by immunostaining. These results indicate that the pancreatic progenitor cells have differentiated into insulin-producing cells. In addition to insulin, increases in mRNA levels were actually observed for Ngn3 and glucose transporter (GLUT2) which are master transcription factors in pancreatic endocrine cells (FIG. 5). Moreover, C-peptide secretion reflecting insulin secretion was also detected (FIG. 5).

Figure 6:
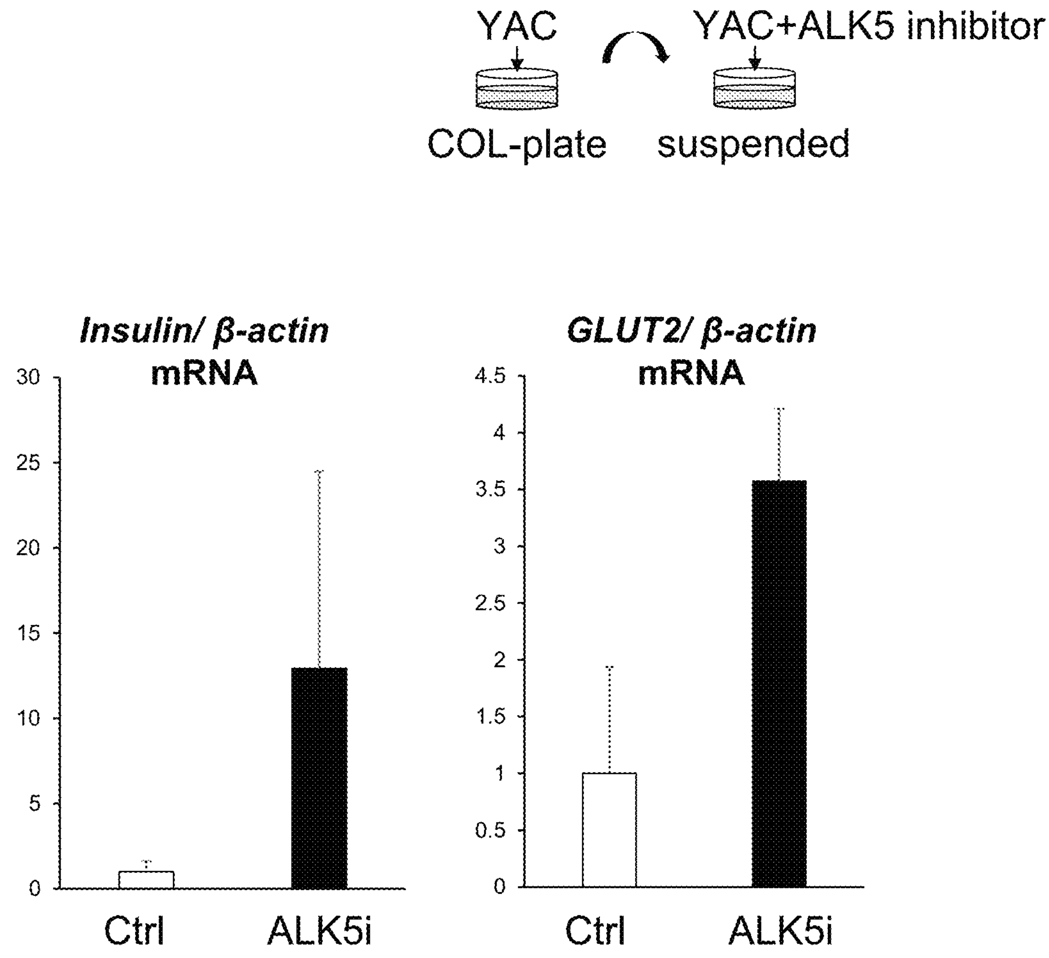
FIG. 6 shows mRNA expression of Insulin and GLUT2.

Likewise, upon floating culture for 7 days in the presence of YAC together with ALK5 inhibitor II (Enzo, ALX-270-445-M001), further improvements were possible in the mRNA expression of Insulin and GLUT2 (FIG. 6).

Figure 7:
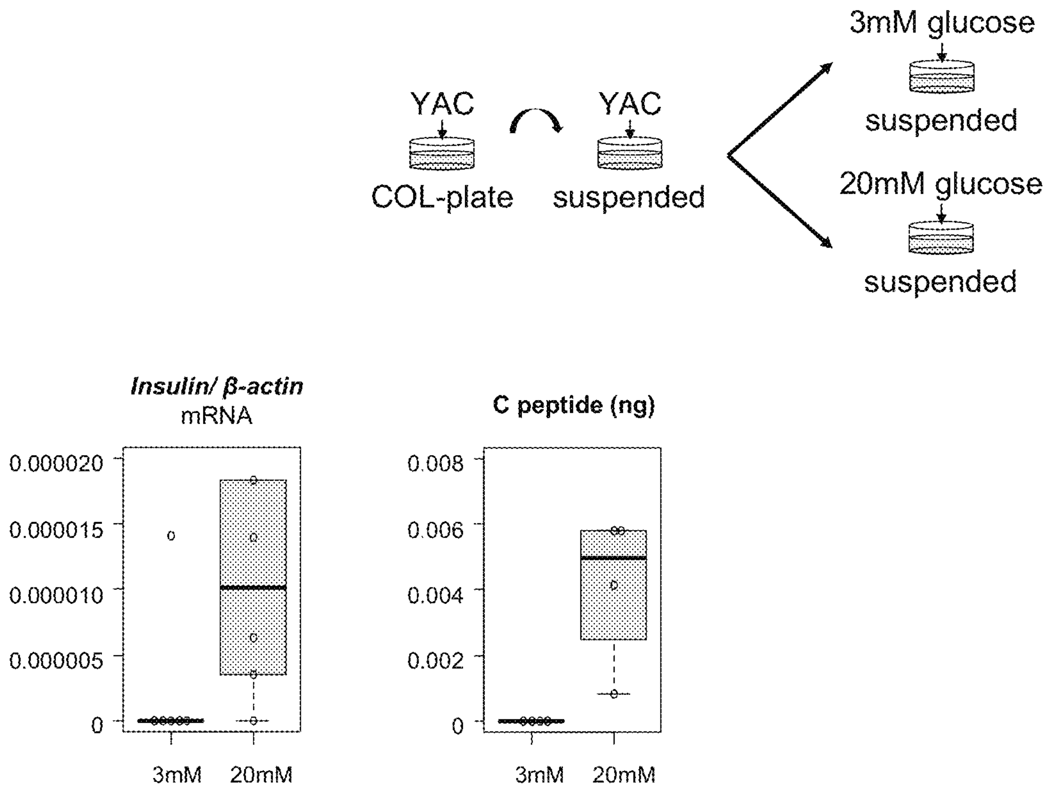
FIG. 7 shows the responsiveness of pancreatic endocrine cells to glucose concentrations.

Furthermore, after induction of differentiation into pancreatic endocrine cells, a comparison was made under conditions of low (3 mM) and high (20 mM) concentrations of glucose in the medium. The high concentration of glucose was found to cause increases in Insulin mRNA and C-peptide in the medium, thus indicating that the pancreatic endocrine cells have acquired the responsiveness to glucose concentrations (FIG. 7).

4) Experiments in Animals

Figure 8:
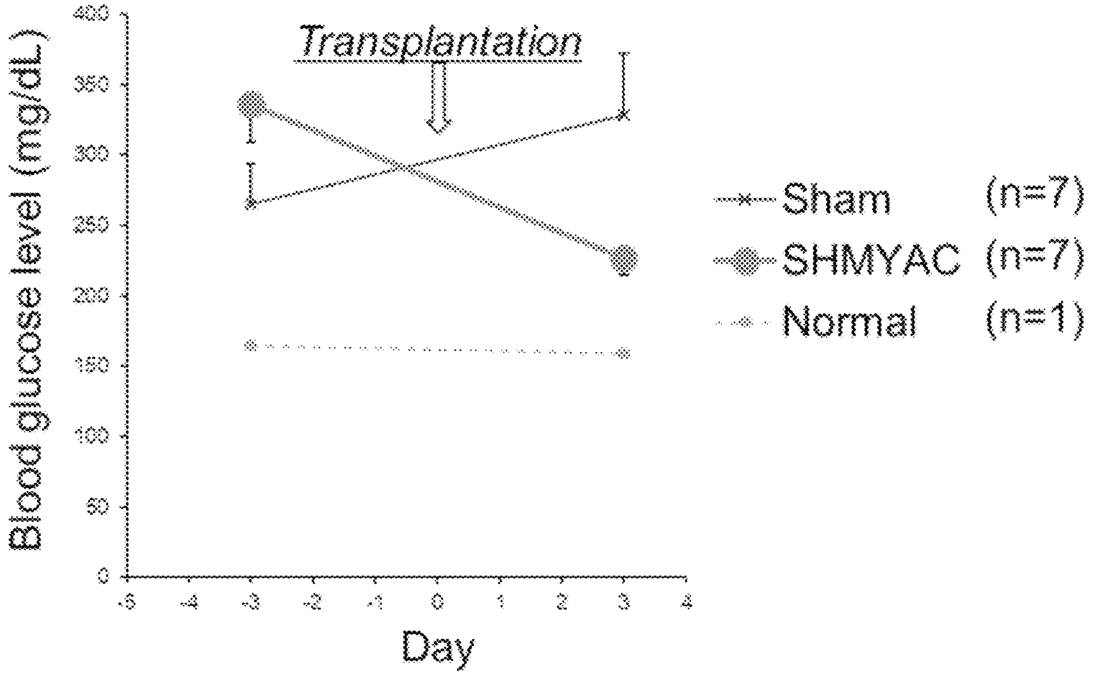
FIG. 8 shows mRNA expression of pancreatic progenitor cell markers after the first passage of subculture.
Figure 9:
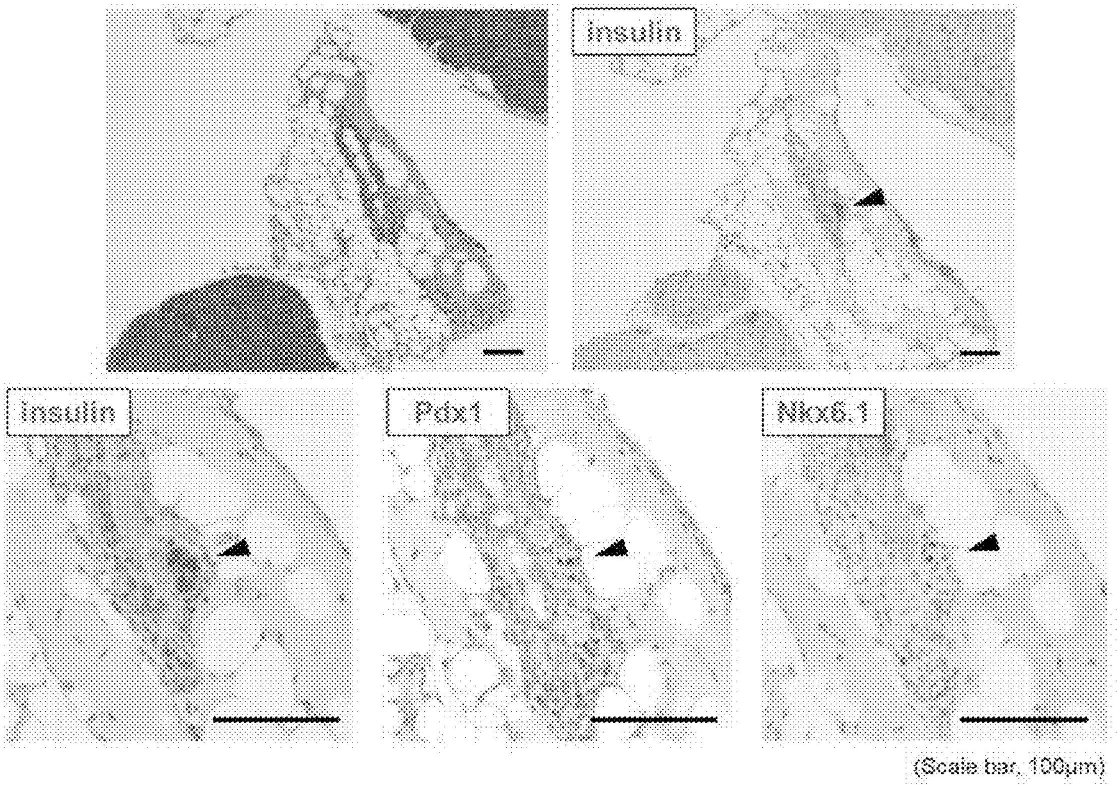
FIG. 9 shows histological images of transplanted cells in an in vivo diabetic environment.

Using streptozotocin-induced diabetic model mice, pancreatic progenitor cells which had been induced to differentiate into insulin-producing cells were encapsulated within Matrigel and transplanted under the pancreatic capsule. As shown in FIG. 8, at 3 days after transplantation, the mice showed improved blood glucose levels. In addition, at the transplantation site, most clusters of the transplanted cells were found to have differentiated into duct-like cells, whereas some of the cells were positive for Insulin, Pdx1 and Nkx6.1 and therefore observed to have differentiated into β cells (FIG. 9).

INDUSTRIAL APPLICABILITY

According to the present invention, pancreatic stem/progenitor cells having self-regeneration ability and differentiation potency (bipotency) into pancreatic exocrine cells can safely and rapidly be induced from pancreatic exocrine cells without genetic modification. The method of the present invention is therefore highly useful in possible applications to a drug-assessing system and pancreatic regenerative medicine.

The invention claimed is:

1. A method of producing pancreatic stem/progenitor cells, the method comprising contacting cells isolated from mammalian pancreas or pancreatic tissue in vitro with a transforming growth factor beta- (TGFβ-) receptor inhibitor, a glycogen synthase kinase 3 (GSK3) inhibitor, and a Rho-associated kinase (ROCK) inhibitor in effective concentrations to form pancreatic stem/progenitor cells.

2. The method of claim 1, wherein the cells isolated from the mammalian pancreas or pancreatic tissue are pancreatic parenchymal cells.

3. The method of claim 1, wherein the cells isolated from the mammalian pancreas or pancreatic tissue are pancreatic exocrine cells selected from the group consisting of acinar cells and pancreatic duct cells.

4. The method of claim 3, wherein the contact between the pancreatic exocrine cells and the TGFβ-receptor inhibitor comprises culturing the pancreatic exocrine cells in the presence of the TGFβ-receptor inhibitor.

5. The method of claim 4, wherein the contact between the pancreatic exocrine cells and the GSK3 inhibitor and the ROCK inhibitor comprises culturing the pancreatic exocrine cells in the presence of the inhibitor(s).

6. The method of claim 1, wherein the cells isolated from the mammalian pancreas or pancreatic tissue are isolated from a human, a rat, or a mouse.

7. The method of claim 1, wherein the pancreatic stem/progenitor cells comprise the following characteristics:

(a) having self-regeneration ability;

(b) are capable of differentiating into pancreatic endocrine cells; and (c) expressing Pdx1, Nkx6.1, Gata4, Hest, Sox9, Foxa2, CK19, and CD133; and (d) do not express and Lgr5.

8. The method of claim 1, further comprising subculturing the pancreatic stem/progenitor cells on a cell-supporting substrate-coated culture vessel in the presence of the TGFβ-receptor inhibitor, the GSK3 inhibitor, and the ROCK inhibitor to maintain or expand the pancreatic stem/progenitor cells.

9. The method of claim 1, further comprising culturing the pancreatic stem/progenitor cells in the presence of the TGFβ-receptor inhibitor, the GSK3 inhibitor, and the ROCK inhibitor to induce the pancreatic stem/progenitor cells into pancreatic endocrine cells.

10. The method of claim 9, further comprising assessing the metabolism of a test compound in a mammalian body comprising:

(i) bringing the test compound into contact with the pancreatic endocrine cells; and (ii) measuring the metabolism of the test compound in the pancreatic endocrine cells.

11. The method of claim 9, further comprising screening for secretion inducers of enzymes secreted from cells comprising:

(i) bringing a test compound into contact with the pancreatic endocrine cells; and (ii) measuring one or more substances secreted in the pancreatic endocrine cells.

12. The method of claim 9, further comprising assessing the endodermal tissue or organ toxicity of a test compound on a mammal comprising:

(i) bringing the test compound into contact with the pancreatic endocrine cells; and (ii) measuring the presence, absence, or the degree of damage in the pancreatic endocrine cells contacted with the test compound.

13. The method of claim 1, further comprising ameliorating pancreatic tissue or organ damage in a mammal comprising administering to a mammal having the tissue or organ damage with an effective amount of the pancreatic stem/progenitor cells.

14. The method of claim 1, wherein the cells isolated from the mammalian pancreas or pancreatic tissue are mature pancreatic cells.

15. The method of claim 1, wherein the method is performed without the use of reprogramming genes.

16. The method of claim 1, wherein the TGFβ-receptor inhibitor is A-83-01, the GSK3 inhibitor is CHIR99021, and the ROCK inhibitor is Y-27632.

17. The method of claim 1, wherein the concentration of A-83-01 ranges from 0.01 μM to 10 μM, the concentration of CHIR99021 ranges from 0.01 μM to 100 μM, and wherein the concentration of Y-27632 ranges from 0.0001 μM to 500 μM.

18. The method of claim 1, wherein the cells isolated from mammalian pancreas or pancreatic tissue are seeded at a cell density ranging from $10^2$ cells/$cm^2$ to $10^6$ cells/$cm^2$.

* * * * *